(12) United States Patent
Wang et al.

(10) Patent No.: US 9,666,110 B2
(45) Date of Patent: May 30, 2017

(54) LIGHTING JIG FOR INSPECTION OF A LIQUID CRYSTAL PANEL

(71) Applicant: BEIJING BOE OPTOELECTRONICS TECHNOLOGY CO., LTD., Beijing (CN)

(72) Inventors: Lei Wang, Beijing (CN); Ziwei Cui, Beijing (CN); Jing Xue, Beijing (CN); Hao Wu, Beijing (CN)

(73) Assignee: BEIJING BOE OPTOELECTRONICS TECHNOLOGY CO., LTD., Beijing (CN)

( * ) Notice: Subject to any disclaimer, the term of this patent is extended or adjusted under 35 U.S.C. 154(b) by 119 days.

(21) Appl. No.: 14/129,340

(22) PCT Filed: Nov. 26, 2012

(86) PCT No.: PCT/CN2012/085251
§ 371 (c)(1),
(2) Date: Dec. 26, 2013

(87) PCT Pub. No.: WO2014/015594
PCT Pub. Date: Jan. 30, 2014

(65) Prior Publication Data
US 2014/0292366 A1     Oct. 2, 2014

(30) Foreign Application Priority Data
Jul. 26, 2012   (CN) .......................... 2012 1 0262873

(51) Int. Cl.
*G09G 3/00*   (2006.01)
*G02F 1/13*   (2006.01)
(Continued)

(52) U.S. Cl.
CPC .......... *G09G 3/006* (2013.01); *G01N 21/8803* (2013.01); *G02F 1/1309* (2013.01); *G01N 2021/9513* (2013.01)

(58) Field of Classification Search
CPC ....... G09G 3/006; G01N 21/88; G02F 1/1309
(Continued)

(56) References Cited

U.S. PATENT DOCUMENTS 5,517,027 A * 5/1996 Nakagawa et al. ............... 850/1
5,872,610 A * 2/1999 Kobayashi .................... 349/139
(Continued)

FOREIGN PATENT DOCUMENTS

| CN | 201654377 | * 11/2010 | ............ G01M 11/02 |
| CN | 201654377 U | 11/2010 | |
| CN | 102789075 A | 11/2012 | |

OTHER PUBLICATIONS

First Chinese Office Action dated Jul. 1, 2014; Appln. No. 201210262873.0.
(Continued)

*Primary Examiner* — Son Le
*Assistant Examiner* — Akm Zakaria
(74) *Attorney, Agent, or Firm* — Ladas & Parry LLP

(57) ABSTRACT

A lighting jig for inspection of a liquid crystal panel, which includes: a base plate; a first supporting plate and a second supporting plate, which are respectively located on and orthogonal to the base plate; and an adsorption platform disposed between the first supporting plate and the second supporting plate and being able to move up and down along a direction orthogonal to the base plate. The adsorption platform has an adsorption surface for adsorbing probes, and the adsorption positions of the probes on the adsorption surface can be adjusted according to distributed locations of circuit test points of various liquid crystal panels to be
(Continued)

inspected. The lighting jig provided by embodiments of the present invention can be used for lighting various types of liquid crystal panels, thereby improving the universality and use efficiency of the lighting jig.

10 Claims, 2 Drawing Sheets

(51) Int. Cl.
  *G01N 21/88* (2006.01)
  *G01N 21/95* (2006.01)
(58) Field of Classification Search
  USPC .................................. 324/755, 756
  See application file for complete search history.

(56) References Cited

U.S. PATENT DOCUMENTS

| | | | |
|---|---|---|---|
| 2002/0107650 A1* | 8/2002 | Wack | G01N 21/211 |
| | | | 702/81 |
| 2004/0155673 A1* | 8/2004 | Liao et al. | 324/770 |
| 2005/0057246 A1* | 3/2005 | Orozco et al. | 324/228 |
| 2005/0184724 A1* | 8/2005 | Huang | G09G 3/006 |
| | | | 324/756.05 |
| 2012/0119773 A1* | 5/2012 | Yu et al. | 324/756.03 |

OTHER PUBLICATIONS

International Preliminary Report on Patentability dated Jan. 27, 2015; PCT/CN2012/085251.
International Search Report mailed Feb. 5, 2013; PCT/CN2012/085251.

\* cited by examiner

LIGHTING JIG FOR INSPECTION OF A LIQUID CRYSTAL PANEL

FIELD OF THE INVENTION

Embodiments of the present invention relate to a lighting jig for inspection of a liquid crystal panel.

BACKGROUND OF THE INVENTION

Currently, in order to meet market demands, a variety of different-sized liquid crystal display devices are developed, which will require a variety of different-sized liquid crystal panels. A liquid crystal panel needs to be analyzed when it comes to failure, and during the analysis, it is necessary to use a lighting jig for lighting the liquid crystal panel, that is, the lighting jig is used to load signals for confirmation. As shown in FIG. 1, during the use of a conventional lighting jig for lighting a liquid crystal panel, the liquid crystal panel 500 is firstly placed onto the lighting jig; then an upper cover 610' of the lighting jig is turned over through rotating about a hinge 620', so that the probes 400 of the upper cover are in contact with the circuit test points of the liquid crystal panel, thereby completing the performance of lighting. Since liquid crystal panels of different sizes have different distributed locations and numbers of circuit test points; and even with the same size, different types of liquid crystal panels still have different distributed locations and numbers of circuit test points; a conventional lighting jig has probes with fixed positions which can not be adjusted; so, liquid crystal panels of each different type will require a corresponding lighting jig, which results in many types of lighting jigs, with each type of lighting jig having a low use efficiency.

SUMMARY OF THE INVENTION

Embodiments of the present invention provide a lighting jig for inspection of a liquid crystal panel, to achieve lighting various types of liquid crystal panels, thereby improving the universality and use efficiency of the lighting jig.

To achieve the above object, the embodiment of the present invention provides a lighting jig for inspection of a liquid crystal panel, the lighting jig comprising: a base plate; a first supporting plate and a second supporting plate, which are respectively located on the base plate and orthogonal to the base plate; and an adsorption platform, which is disposed between the first supporting plate and the second supporting plate, and is able to move up and down along a direction orthogonal to the base plate; the adsorption platform has an adsorption surface for adsorbing probes, and the adsorption positions of the probes on the adsorption surface can be adjusted according to distributed locations of circuit test points of various liquid crystal panels to be inspected.

In another embodiment of the present invention, the lighting jig can further comprise: a third supporting plate, which is orthogonal to the base plate and intersects orthogonally with the first supporting plate and the second supporting plate; and the adsorption platform is disposed between the first supporting plate, the second supporting plate and the third supporting plate.

In further another embodiment of the present invention, a portion of the adsorption surface can be orthogonal to the plane where the base plate lies and orthogonal to the plane where the first supporting plate lies.

In yet another embodiment of the present invention, the adsorption platform can comprise a through-hole penetrating from top to bottom, and the adsorption surface is all or part of the inner surface of the through-hole.

In yet another embodiment of the present invention, the through-hole can be a through-hole with an "H"-shaped cross-section, and the inner surfaces of the two mutually parallel "|"-shaped parts of the "H"-shaped through-hole are orthogonal to the plane where the base plate lies and orthogonal to the plane where the first supporting plate lies;
  or, the through-hole can be a through-hole with a rectangular cross-section, and the inner surfaces of the two long sides of the rectangular through-hole are orthogonal to the plane where the base plate lies and orthogonal to the plane where the first supporting plate lies;
  or, the through-hole can be a through-hole with a "⌊"-shaped or "⌋"-shaped cross-section, and the inner surface of the transverse side of the "⌊"-shaped or "⌋"-shaped through-hole is orthogonal to the plane where the base plate lies and orthogonal to the plane where the first supporting plate lies;
  or, the through-hole can be a through-hole with an inverted-"T"-shaped cross-section, and the inner surface of the transverse side of the inverted-"T"-shaped through-hole is orthogonal to the plane where the base plate lies and orthogonal to the plane where the first supporting plate lies.

In yet another embodiment of the present invention, the first supporting plate and/or the second supporting plate is provided with a groove extending from top to bottom at its lateral surface engaging with the adsorption platform, whereas the adsorption platform is provided with a slider at its lateral surface engaging with the first supporting plate and/or the second supporting plate, and the adsorption platform is engaged between the first supporting plate and the second supporting plate by catching the slider in the groove.

In yet another embodiment of the present invention, the third supporting plate is provided with a groove extending from top to bottom at its lateral surface engaging with the adsorption platform, whereas the adsorption platform is provided with a slider at its lateral surface engaging with the third supporting plate, and the adsorption platform is engaged onto the third supporting plate by catching the slider in the groove.

In yet another embodiment of the present invention, the adsorption platform is provided thereon with a handle.

In yet another embodiment of the present invention, the adsorption platform is a magnetic adsorption platform, and the probes are probes with magnetic attraction to the magnetic adsorption platform.

In yet another embodiment of the present invention, the adsorption platform is provided with upper-and-lower two fixing holes at its lateral surface engaging with the first supporting plate and/or the second supporting plate, whereas the first supporting plate and/or the second supporting plate is provided with a fixing bolt at its lateral surface, and the fixing bolt can be respectively caught in the fixing hole.

With the lighting jig provided by the embodiment of the present invention for inspection of a liquid crystal panel, when the lighting jig is used for lighting a liquid crystal panel, the liquid crystal panel is placed onto the base plate, so that the circuit test points of the liquid crystal panel get through the space between the first supporting plate and the second supporting plate and reach beneath the adsorption platform, and probes in the same number as the circuit test points are adsorbed onto the adsorption surface; by adjusting the positions of the probes and the liquid crystal panel, the probes are positioned corresponding to the circuit test points of the liquid crystal panel to be inspected, that is, the probes are in testing positions; by moving the adsorption platform downwards, the probes are brought into contact with the circuit test points of the liquid crystal panel, thus lighting is achieved.

BRIEF DESCRIPTION OF THE DRAWINGS

In order to clearly illustrate the technical solutions of the embodiments of the invention, the drawings of the embodiments will be briefly described in the following; it is obvious that the described drawings are only related to some embodiments of the invention and thus are not limitative of the invention.

DETAILED DESCRIPTION OF THE PREFERRED EMBODIMENTS

Figure 1:
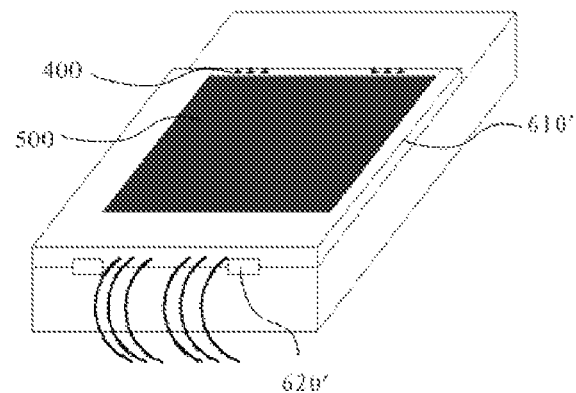
FIG. 1 is a schematic diagram of the working principle of an existing lighting jig for lighting a liquid crystal panel.

In order to make objects, technical details and advantages of the embodiments of the invention apparent, the technical solutions of the embodiments will be described in a clearly and fully understandable way in connection with the drawings related to the embodiments of the invention. It is obvious that the described embodiments are just a part but not all of the embodiments of the invention. Based on the described embodiments herein, those skilled in the art can obtain other embodiment(s), without any inventive work, which should be within the scope of the invention.

The lighting jig according to a first embodiment of the present invention, for inspection of a liquid crystal panel, comprises: a base plate; a first supporting plate and a second supporting plate, which are respectively located on the base plate and orthogonal to the base plate; and an adsorption platform, which is disposed between the first supporting plate and the second supporting plate, and is able to move up and down along a direction orthogonal to the base plate. The adsorption platform has an adsorption surface for adsorbing probes, and the adsorption positions of the probes on the adsorption surface can be adjusted according to distributed locations of circuit test points of various liquid crystal panels to be inspected, wherein the probes are connected via signal lines with the circuit section of the lighting jig.

The connection form for disposing the adsorption platform between the first supporting plate and the second supporting plate, can be a snap-connection, and also can be other connection forms, as long as it can achieve a movable connection of the adsorption platform between the first supporting plate and the second supporting plate and an up and down movement of the adsorption platform along a direction orthogonal to the base plate.

With the lighting jig of the embodiment for inspection of a liquid crystal panel, when the lighting jig is used for lighting a liquid crystal panel, the liquid crystal panel is placed onto the base plate, so that the circuit test points of the liquid crystal panel get through the space between the first supporting plate and the second supporting plate and reach beneath the adsorption platform, and probes in the same number as the circuit test points are adsorbed onto the adsorption surface; by adjusting the positions of the probes and the liquid crystal panel, the adsorbed probes are positioned corresponding to the circuit test points of the liquid crystal panel to be inspected, that is, the probes are in testing positions; by moving the adsorption platform downwards, the probes are brought into contact with the circuit test points of the liquid crystal panel, and thus lighting is achieved. When using the lighting jig of the embodiment of the present invention for lighting, only by adjusting its probes in the same number as the circuit test points into testing positions, lighting various types of liquid crystal panels can be achieved. In this way, lighting various types of liquid crystal panels can be achieved with the lighting jig of the embodiment of the present invention, thereby reducing costs and improving use efficiency.

In a second embodiment of the present invention, the lighting jig can further comprise: a third supporting plate, which is orthogonal to the base plate and intersects orthogonally with the first supporting plate and the second supporting plate; and the adsorption platform is disposed between the first supporting plate, the second supporting plate and the third supporting plate.

The connection form for disposing the adsorption platform onto the third supporting plate, can be a snap-connection, and also can be other connection forms, as long as it can achieve a movable connection of the adsorption platform with the third supporting plate and an up and down movement of the adsorption platform along a direction orthogonal to the base plate.

In a third embodiment of the present invention, a portion of the adsorption surface is orthogonal to the plane where the base plate lies and orthogonal to the plane where the first supporting plate lies. For convenience of description, such portion of the adsorption surface that is orthogonal to the plane where the base plate lies and orthogonal to the plane where the first supporting plate lies, is defined as a first adsorption surface.

In a fourth embodiment of the present invention, the adsorption platform comprises a through-hole penetrating from top to bottom, and the adsorption surface is all or part of the inner surface of the through-hole.

In a fifth embodiment of the present invention, the first preferred mode is that: the through-hole can be a through-hole with an "H"-shaped cross-section, and the inner surfaces of the two mutually parallel "|"-shaped parts of the "H"-shaped through-hole are orthogonal to the plane where the base plate lies and orthogonal to the plane where the first supporting plate lies;

that is, the adsorption surface is the entire inner surface of the "H"-shaped through-hole, and the first adsorption surface is the inner surfaces of the two mutually parallel "|"-shaped parts of the "H"-shaped through-hole;

or, the adsorption surface is part of the inner surface of the "H"-shaped through-hole, and the first adsorption surface is the inner surface(s) of either or both of the two mutually parallel "|"-shaped parts of the "H"-shaped through-hole.

It should be noted that, the two "|"-shaped parts of the "H"-shaped through-hole preferably have the same structure, i.e., have the same length. Of course, the case in which they have different lengths, for instance, one is longer and the other is shorter, also falls within the scope of the present invention.

The second preferred mode is that: the through-hole is a through-hole with a rectangular cross-section, and the inner surfaces of the two long sides of the rectangular through-hole are orthogonal to the plane where the base plate lies and orthogonal to the plane where the first supporting plate lies;

that is, the adsorption surface is the entire inner surface of the rectangular through-hole, and the first adsorption surface is the inner surfaces of the two long sides of the rectangular through-hole;

or, the adsorption surface is part of the inner surface of the rectangular through-hole, and the first adsorption surface is the inner surface(s) of either or both of the two long sides of the rectangular through-hole.

The third preferred mode is that: the through-hole is a through-hole with a "["-shaped or "]"-shaped cross-section, and the inner surface of the transverse side of the "["-shaped or "]"-shaped through-hole is orthogonal to the plane where the base plate lies and orthogonal to the plane where the first supporting plate lies;

that is, the adsorption surface is the inner surface of the "["-shaped or "]"-shaped through-hole, and the first adsorption surface is the inner surface of the transverse side of the "["-shaped or "]"-shaped through-hole.

The fourth preferred mode is that: the through-hole is a through-hole with an inverted-"T"-shaped cross-section, and the inner surface of the transverse side of the inverted-"T"-shaped through-hole is orthogonal to the plane where the base plate lies and orthogonal to the plane where the first supporting plate lies;

That is, the adsorption surface is the inner surface of the inverted-"T"-shaped through-hole, and the first adsorption surface is the inner surface of the transverse side of the inverted-"T"-shaped through-hole.

Of course, the shape of the through-hole is not limited to the four preferred modes described above, and can also be a through-hole in other shapes, as long as the cross-sectional shape of the through-hole can achieve that the first adsorption surface is orthogonal to the plane where the base plate lies and orthogonal to the plane where the first supporting plate lies, which herein is merely explained by way of example.

In a sixth embodiment of the present invention, the first supporting plate and/or the second supporting plate is provided with a groove extending from top to bottom at its lateral surface opposing the adsorption platform, whereas the adsorption platform is provided with a slider at its lateral surface opposing the first supporting plate and/or the second supporting plate, and the adsorption platform is engaged between the first supporting plate and the second supporting plate by catching the slider in the groove.

The groove can be provided only on the first supporting plate, or can be provided only on the second supporting plate, or can be provided on both the first supporting plate and the second supporting plate. Of course, accordingly, the adsorption platform is provided with a slider at its lateral side opposing a supporting plate provided with a groove.

In a seventh embodiment of the present invention, the third supporting plate is provided with a groove extending from top to bottom at its lateral surface opposing the adsorption platform, whereas the adsorption platform is provided with a slider at its lateral surface opposing the third supporting plate, and the adsorption platform is engaged to the third supporting plate by catching the slider into the groove.

In an eighth embodiment of the present invention, the adsorption platform is provided on its upper surface with a handle for easy grip.

In a ninth embodiment of the present invention, the adsorption platform is a magnetic adsorption platform, and the probes are probes with magnetic attraction to the magnetic adsorption platform. For example, the adsorption platform is a ferromagnetic adsorption platform, and the probes are ferrous probes.

In a tenth embodiment of the present invention, the adsorption platform is provided with an upper and a lower fixing holes at its lateral surface engaging with the first supporting plate and/or the second supporting plate, whereas the first supporting plate and/or the second supporting plate is provided with a fixing bolt at its lateral surface, and the fixing bolt can be respectively caught in the fixing hole.

The above is the description of the technical solutions in the embodiments of the present invention. Of course, the embodiments of the present invention can also be any combinations of the technical solutions, which are all within the scope of the present invention.

Figure 2:
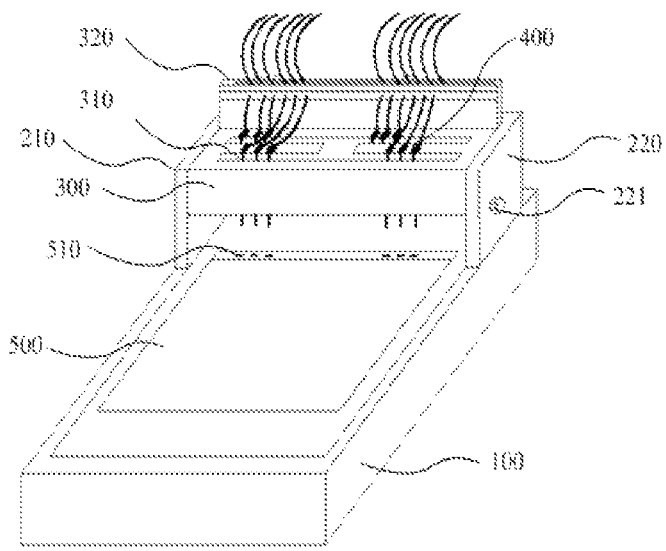
FIG. 2 is a schematic diagram of a lighting jig according to an embodiment of the present invention, for lighting a liquid crystal panel in inspection.
Figure 3:
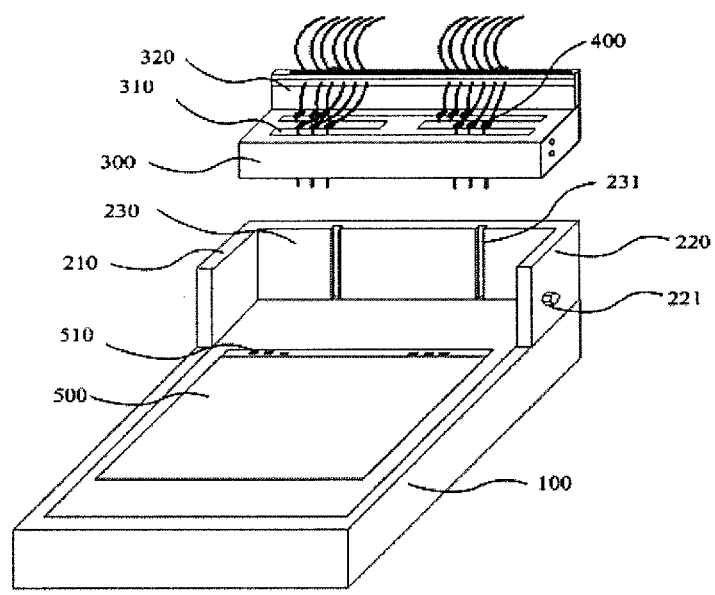
FIG. 3 is an exploded schematic structural diagram of the lighting jig shown in FIG. 2.

FIG. 2 and FIG. 3 illustrate the lighting jig according to one embodiment of the present invention for inspection of a liquid crystal panel, and the lighting jig comprises: a base plate 100; a first supporting plate 210, a second supporting plate 220 and a third supporting plate 230, which are orthogonal to the base plate 100 at one end of the base plate 100; wherein the first supporting plate 210 and the second supporting plate 220 are mutually parallel, whereas the third supporting plate 230 intersects orthogonally with the first supporting plate 210 and the second supporting plate 220.

An adsorption platform 300 is engaged between the first supporting plate 210, the second supporting plate 220 and the third supporting plate 230. The adsorption platform 300 can move up and down along the first supporting plate 210, the second supporting plate 220 and the third supporting plate 230. The adsorption platform 300 comprises a through-hole 310 with an "H"-shaped cross-section, penetrating the adsorption platform 300 from top to bottom. The inner surfaces of the two mutually parallel "|"-shaped parts of the "H"-shaped through-hole 310, are parallel to the plane where the third supporting plate 230 lies.

The adsorption platform 300 is an adsorption platform made of a ferromagnetic material, for adsorbing probes. The probes can be ferrous probes, which can be adsorbed on the inner surface of the "H"-shaped through-hole 310. That is, the inner surface of the "H"-shaped through-hole 310 is the adsorption surface for adsorbing probes, and the inner surfaces of the two mutually parallel "|"-shaped parts of the "H"-shaped through-hole 310 are the first adsorption surface.

Further, as shown in FIG. 3, the third supporting plate 230 is provided with a groove 231 extending from top to bottom at its lateral surface engaging with the adsorption platform 300, whereas the adsorption platform is provided with a slider at its lateral surface engaging with the third supporting plate, and the adsorption platform is snap-connected with the third supporting plate by catching the slider in the groove 231.

Further, as shown in FIG. 2 and FIG. 3, the adsorption platform is provided on its upper surface with a handle 320 for easy grip.

As shown in FIG. 2, before the lighting jig of the embodiment is used for lighting, all probes 400 are adsorbed on the inner surface of the "|"-shaped part at the end of the "H"-shaped through-hole 310 near the third supporting plate. Now, the probes are in initial positions. The process of using the lighting jig of the embodiment for lighting is as follows:

Firstly, the number and the positions of the circuit test points 510 of the liquid crystal panel 500 are checked, and the liquid crystal panel 500 is placed on the base plate 100, so that the circuit test points 510 of the liquid crystal panel are located beneath the "|"-shaped part of the "H"-shaped through-hole 310 far from the third supporting plate. As shown in FIG. 2, the circuit test points 510 of the liquid crystal panel are the 6 circuit test points, i.e., 3 circuit test points on each of the right side and the left side.

Secondly, the number of the probes is choosed according to the circuit test points 510 of the liquid crystal panel, and the probes are held above the circuit test points of the liquid crystal panel. As shown in FIG. 2, the 6 probes are moved along the vertical portion of the "H"-shaped through-hole 310, to the "|"-shaped part of the "H"-shaped through-hole far from the third supporting plate, and adsorbed on the inner surface, and thus the 6 probes are held above the circuit test points 510 of the liquid crystal panel. Now, the probes are in testing positions;

Then, by using the handle 320 to move the adsorption platform 300 downwards, the probes 400 are brought into contact with the circuit test points 510 of the liquid crystal panel, thus achieving lighting.

Various types of liquid crystal panels can have different distributed locations and numbers of circuit test points. However, when using the lighting jig of the embodiment for lighting a liquid crystal panel in inspection, by only adjusting its probes in the same number as the circuit test points from initial positions into testing positions, and then bringing the probes into contact with the circuit test points of the liquid crystal panel, the lighting jig can thus achieve lighting various types of liquid crystal panels. In this way, lighting various types of liquid crystal panels can be achieved with the lighting jig of the embodiment of the present invention, thereby reducing costs and improving use efficiency.

Further, as shown in FIG. 3, the adsorption platform 300 can be provided with upper-and-lower two fixing holes at its lateral surface engaging with the second supporting plate 220, whereas the second supporting plate 220 is provided with a fixing bolt 221 at its lateral surface, and the fixing bolt 221 can be respectively caught in the fixing hole. By catching the fixing bolt 221 in different fixing holes, the adsorption platform is kept from the base plate by different distances. When the probes are in initial positions, the fixing bolt 221 is caught in the upper fixing hole, so that the adsorption platform has a larger distance from the base plate; after the probes are brought into contact with the circuit test points of a liquid crystal panel, the fixing bolt 221 is caught in the lower fixing hole, so that the probes are kept in contact with the circuit test points of the liquid crystal panel, and it is ensured that the adsorption platform will not squeeze the liquid crystal panel.

In addition, the through-hole can also be, for example, a through-hole with a rectangular cross-section; and in this case, the adsorption surface is all or part of the inner surface of the rectangular through-hole, and the first adsorption surface is the inner surfaces of the long sides of the rectangular through-hole.

For example, in another embodiment, the adsorption platform is an adsorption platform made of a ferromagnetic material, and the adsorption surface is the entire inner surface of a rectangular through-hole, and the first adsorption surface is the inner surfaces of the long sides of the rectangular through-hole. When the probes are located in initial positions, the probes are adsorbed on the inner surface of the long sides of the rectangular through-hole far from the circuit test points of a liquid crystal panel; when the probes are located in testing positions, the probes are adsorbed on the inner surface of the long sides of the rectangular through-hole near the circuit test points of the liquid crystal panel.

In addition, the adsorption platform can also be an adsorption platform not made of a ferromagnetic material; and in this case, an adsorption surface for adsorbing probes can be formed on all or part of the inner surface of a rectangular through-hole, and the adsorption surface comprises such a portion that is orthogonal to the plane where the base plate lies and orthogonal to the plane where the first supporting plate lies, i.e., the first adsorption surface. For example, the adsorption surface comprises both the inner surface of either short side of a rectangular through-hole and the inner surface of the long sides of the rectangular through-hole near the circuit test points of a liquid crystal panel, then the first adsorption surface is said inner surface of the long sides of the rectangular through-hole near the circuit test points of the liquid crystal panel. And for example, both the inner surfaces of the two long sides of a rectangular through-hole are the adsorption surface, and also the first adsorption surface.

As an alternative mode, the through-hole is a through-hole with a "⌊"-shaped "⌋"-shaped cross-section; and in this case, the adsorption surface is the inner surface of the "⌊"-shaped or "⌋"-shaped through-hole, and the first adsorption surface is the inner surface of the transverse side of the "⌊"-shaped or "⌋"-shaped through-hole. When the probes are in initial positions, the probes are adsorbed on the inner surface of the vertical side of the "⌊"-shaped or "⌋"-shaped through-hole; and when the probes are in testing positions, the probes are adsorbed on the inner surface of the transverse side of the "⌊"-shaped or "⌋"-shaped through-hole.

As an optional mode, the through-hole is a through-hole with an inverted-"T"-shaped cross-section; and in this case, the adsorption surface is the inner surface of the inverted-"T"-shaped through-hole, and the first adsorption surface is the inner surface of the transverse side of the inverted-"T"-shaped through-hole. When the probes are in initial positions, the probes are adsorbed on the inner surface of the vertical side of the inverted-"T"-shaped through-hole; and when the probes are in testing positions, the probes are adsorbed on the inner surface of the transverse side of the inverted-"T"-shaped through-hole.

When using the lighting jig of the embodiment of the present invention for lighting, by only adjusting its probes in the same number as the circuit test points into testing positions, it can achieve lighting various types of liquid crystal panels. In this way, lighting various types of liquid crystal panels can be achieved with the lighting jig of the embodiment of the present invention, thereby reducing costs and improving use efficiency.

The above are merely exemplary implementations of the present invention, but not for limiting the scope of the invention; instead, the scope of the invention should be defined by the appended claims.

What is claimed is:

1. A lighting jig for inspection of a liquid crystal panel, comprising:
   a base plate;
   a first supporting plate and a second supporting plate, which are respectively located on the base plate and orthogonal to the base plate;
   a third supporting plate which is orthogonal to the base plate and intersects orthogonally with the first supporting plate and the second supporting plate; and
   an adsorption platform, which is disposed between the first supporting plate, the second supporting plate and the third supporting plate, and is able to move up and down along a direction orthogonal to the base plate; the adsorption platform has an adsorption surface for adsorbing probes, and adsorption positions of the probes on the adsorption surface can be adjusted according to distributed locations of circuit test points of various liquid crystal panels to be inspected, wherein the third supporting plate is provided with a groove extending from top to bottom at its lateral surface opposing the adsorption platform, whereas the adsorption platform is provided with a slider at its lateral surface opposing the third supporting plate, and the adsorption platform is engaged onto the third supporting plate by catching the slider in the groove, and wherein the adsorption platform is a magnetic adsorption platform, and the probes are probes with magnetic attraction to the magnetic adsorption platform.

2. The lighting jig according to claim 1, wherein a portion of the adsorption surface is orthogonal to a plane where the base plate lies and orthogonal to the plane where the first supporting plate lies.

3. The lighting jig according to claim 2, wherein the adsorption platform comprises a through-hole penetrating from top to bottom, and the adsorption surface is all or part of an inner surface of the through-hole.

4. The lighting jig according to claim 3, wherein the through-hole is a through-hole with an "H"-shaped cross-section, and the inner surfaces of the two mutually parallel "|"-shaped parts of the "H"-shaped through-hole are orthogonal to the plane where the base plate lies and orthogonal to the plane where the first supporting plate lies;

or, the through-hole is a through-hole with a rectangular cross-section, and the inner surfaces of the two long sides of the rectangular through-hole are orthogonal to the plane where the base plate lies and orthogonal to the plane where the first supporting plate lies;

or, the through-hole is a through-hole with a "["-shaped or "]"-shaped cross-section, and the inner surface of the transverse side of the "["-shaped or "]"-shaped through-hole is orthogonal to the plane where the base plate lies and orthogonal to the plane where the first supporting plate lies;

or, the through-hole is a through-hole with an inverted-"T"-shaped cross-section, and the inner surface of the transverse side of the inverted-"T"-shaped through-hole is orthogonal to the plane where the base plate lies and orthogonal to the plane where the first supporting plate lies.

5. The lighting jig according to claim 3, wherein the first supporting plate and/or the second supporting plate is provided with a groove extending from top to bottom at its lateral surface opposing the adsorption platform, whereas the adsorption platform is provided with a slider at its lateral surface opposing the first supporting plate and/or the second supporting plate, and the adsorption platform is engaged between the first supporting plate and the second supporting plate by catching the slider in the groove.

6. The lighting jig according to claim 1, wherein the adsorption platform is provided thereon with a handle.

7. The lighting jig according to claim 1, wherein the adsorption platform is provided with an upper and a lower fixing holes at its lateral surface engaging with the first supporting plate and/or the second supporting plate, whereas the first supporting plate and/or the second supporting plate is provided with a fixing bolt at its lateral surface, and the fixing bolt can be respectively caught in the fixing hole.

8. The lighting jig according to claim 4, wherein the first supporting plate and/or the second supporting plate is provided with a groove extending from top to bottom at its lateral surface opposing the adsorption platform, whereas the adsorption platform is provided with a slider at its lateral surface opposing the first supporting plate and/or the second supporting plate, and the adsorption platform is engaged between the first supporting plate and the second supporting plate by catching the slider in the groove.

9. The lighting jig according to claim 8, wherein the adsorption platform is provided thereon with a handle.

10. The lighting jig according to claim 8, wherein the adsorption platform is provided with an upper and a lower fixing holes at its lateral surface engaging with the first supporting plate and/or the second supporting plate, whereas the first supporting plate and/or the second supporting plate is provided with a fixing bolt at its lateral surface, and the fixing bolt can be respectively caught in the fixing hole.

* * * * *